(12) United States Patent
Hsieh et al.

(10) Patent No.: US 8,831,180 B2
(45) Date of Patent: Sep. 9, 2014

(54) APPARATUS FOR SCATTER REDUCTION FOR CT IMAGING AND METHOD OF FABRICATING SAME

(75) Inventors: Jiang Hsieh, Brookfield, WI (US); Thomas Murray Leeds, Pewaukee, WI (US); Abdelaziz Ikhlef, Hartland, WI (US)

(73) Assignee: General Electric Company, Schenectady, NY (US)

( * ) Notice: Subject to any disclaimer, the term of this patent is extended or adjusted under 35 U.S.C. 154(b) by 448 days.

(21) Appl. No.: 13/198,283

(22) Filed: Aug. 4, 2011

(65) Prior Publication Data
US 2013/0034200 A1   Feb. 7, 2013

(51) Int. Cl.
*G21K 1/04*  (2006.01)
*G21K 1/02*  (2006.01)
*G21K 1/00*  (2006.01)
*A61B 6/00*  (2006.01)
*A61B 6/03*  (2006.01)
*A61N 5/10*  (2006.01)

(52) U.S. Cl.
CPC .............. *A61N 5/10* (2013.01); *A61B 6/4014* (2013.01); *G21K 1/025* (2013.01); *A61B 6/032* (2013.01); *A61B 6/482* (2013.01); *A61B 6/4291* (2013.01); *A61B 6/03* (2013.01)
USPC ................................ 378/149; 378/19; 378/150

(58) Field of Classification Search
CPC ............. G21K 1/00; G21K 1/02; G21K 1/04; H05G 1/02
USPC ................. 378/4–20, 147, 149, 150, 204, 210
See application file for complete search history.

(56) References Cited

U.S. PATENT DOCUMENTS

| | | | |
|---|---|---|---|
| 7,149,284 B2 | 12/2006 | Ikhlef | |
| 7,397,887 B2 * | 7/2008 | Kuhn | 378/9 |
| 7,564,940 B2 | 7/2009 | Mattson et al. | |
| 7,611,990 B2 * | 11/2009 | Yoon et al. | 438/680 |
| 2008/0101542 A1 | 5/2008 | Ikhlef et al. | |
| 2008/0165922 A1 * | 7/2008 | Yanoff et al. | 378/19 |

* cited by examiner

*Primary Examiner* — Anastasia Midkiff
(74) *Attorney, Agent, or Firm* — Ziolkowski Patent Solutions Group, SC

(57) ABSTRACT

A collimator for an imaging system includes a first region comprising a first one-dimensional array of apertures along a channel direction, and a second region comprising a second one-dimensional array of apertures along the channel direction, wherein an aspect ratio of the apertures of the first region is greater than an aspect ratio of the second region.

31 Claims, 10 Drawing Sheets

APPARATUS FOR SCATTER REDUCTION FOR CT IMAGING AND METHOD OF FABRICATING SAME

BACKGROUND OF THE INVENTION

Embodiments of the invention relate generally to diagnostic imaging and, more particularly, to an apparatus for scatter reduction for CT imaging and a method of fabricating same.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotating about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

In recent years CT systems have increasing z-coverage in order to shorten scan times and reduce overall dose. The goal has been to obtain an image of an object, such as a cardiac region, in a single rotation. As CT systems have grown in z-coverage (i.e., increased numbers of slices), however, scatter has become an increasingly significant factor. For example, for a 16-slice scanner with 10 mm z-coverage, the scatter-to-primary ratio (SPR) is less than 10% for a 35 cm poly phantom. When the z-coverage increases to 40 mm (or 64 slices), the SPR increases to 20% for the same size phantom. It is well-known that an increased SPR degrades image quality due to image artifact and noise increase.

Many attempts have been made in the past to improve the scatter performance of CT systems. For example, by increasing the aspect ratio of post-patient collimation plates, the scatter rejection capability can be significantly improved. The aspect ratio for a collimator is typically defined as the collimator plate height (H) divided by the aperture width (W). In general, the higher the aspect ratio, the better is the scatter rejection capability. However, as known in the art, the scatter rejection capability of a one-dimensional (1D) configuration is limited since scattered radiation in the y-z plane can still reach the detector without being blocked.

To overcome the shortcomings of 1D collimation, two-dimensional (2D) collimation may be used in order to improve the scatter rejection capability of the system. In such a configuration, collimator plates are placed orthogonal to each other and all point (or focus) to the x-ray focal spot, in order to block the scattered radiation in this direction. It has been shown that with the additional collimation, the SPR can be reduced to less than 10% for a 16 cm z-coverage system using a 35 cm poly phantom. The drawback of this approach, however, is a significant increase in the cost to the design and manufacturing.

Therefore, it would be desirable to design an apparatus and method of fabricating a collimator to reduce an amount of scatter and reduce overall cost of an imaging system.

BRIEF DESCRIPTION OF THE INVENTION

The invention is a directed apparatus for collimating x-rays in an imaging system and a method of fabricating same.

According to one aspect, a collimator for an imaging system includes a first region comprising a first one-dimensional array of apertures along a channel direction, and a second region comprising a second one-dimensional array of apertures along the channel direction, wherein an aspect ratio of the apertures of the first region is greater than an aspect ratio of the second region.

According to another aspect, a method of forming a collimator for an imaging system includes forming a first one-dimensional array of apertures, forming a second one-dimensional array of apertures having an aspect ratio that is different from that of the first one-dimensional array of apertures, and attaching the first one-dimensional array of apertures and the second one-dimensional array of apertures to a support structure.

According to yet another aspect, a CT system includes a rotatable gantry having an opening to receive an object to be scanned, a first high frequency electromagnetic energy projection source configured to project a high frequency electromagnetic energy beam toward the object, a first scintillator array having a plurality of scintillator cells wherein each cell is configured to detect high frequency electromagnetic energy passing through the object, and a first photodiode array optically coupled to the scintillator array and comprising a plurality of photodiodes configured to detect light output from a corresponding scintillator cell. The system includes an image reconstructor coupled to the first photodiode array and configured to reconstruct an image of the object from the first photodiode array outputs, and a first collimator positioned between the first high frequency electromagnetic energy projection source and the scintillator. The first collimator includes a first sub-assembly comprised of a first one-dimensional array of openings, and a second sub-assembly comprised of a second one-dimensional array of openings, wherein an aspect ratio of the second one-dimensional array of openings is less than an aspect ratio of the first one-dimensional array of openings. The system also includes a computer programmed to obtain imaging data of the object, and reconstruct an image of the object using the imaging data.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION OF THE PREFERRED EMBODIMENT

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
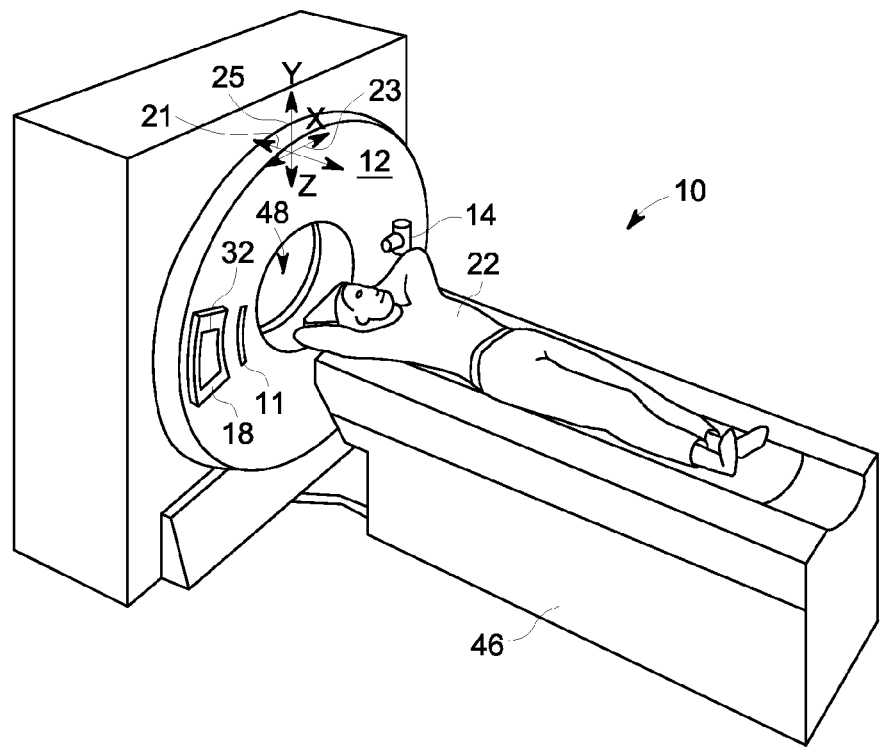
FIG. 1 is a pictorial view of a CT imaging system.
Figure 2:
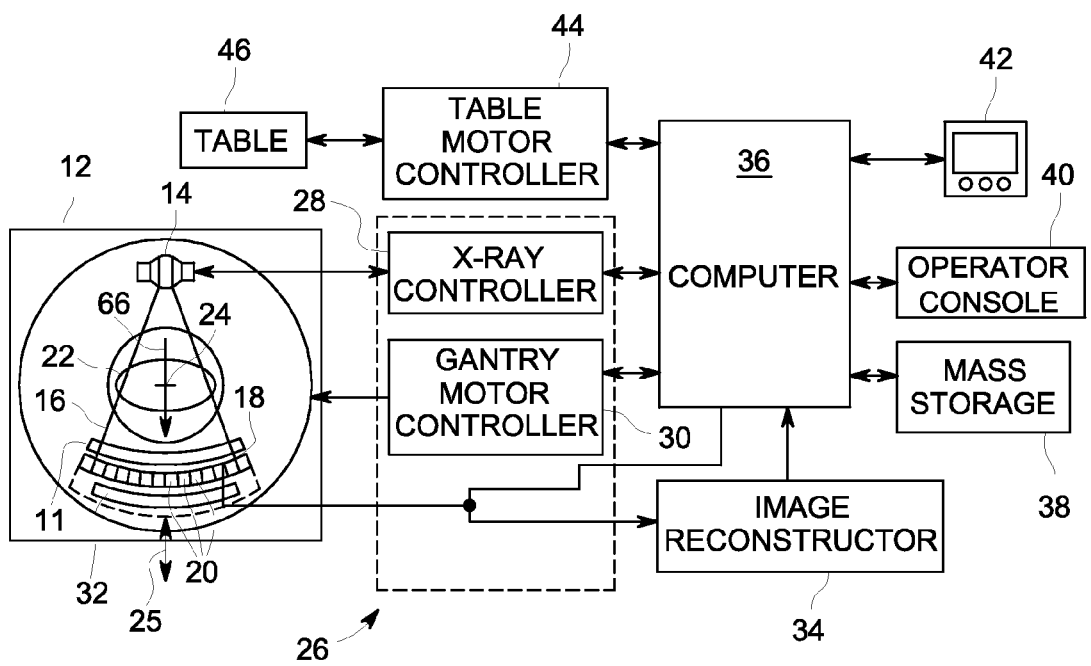
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 through a collimator assembly 11 and toward a detector assembly 18 on the opposite side of the gantry 12. Collimator assembly 11 is illustrated as a post-patient collimator that is positioned, when imaging, between a medical patient 22 and detector assembly 18. Detector assembly 18 is formed by a plurality of detectors 20 and data acquisition systems (DAS) 32. The plurality of detectors 20 sense the projected x-rays 16 that pass through medical patient 22 and are collimated by collimator assembly 11. DAS 32 converts the data from detectors 20 to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

As commonly understood in the art, patient 22 is generally translated along a z-direction 21, or slice-direction, of gantry 12. As also commonly understood in the art, detector assembly 18 is caused to rotate circumferentially in an x-direction 23, or channel direction, of gantry 12. Thus, x-rays 16 travel generally in a y-direction 25, through collimator 11, and through detector assembly 18, as they emit from x-ray source 14 and pass through patient 22.

Figure 3:
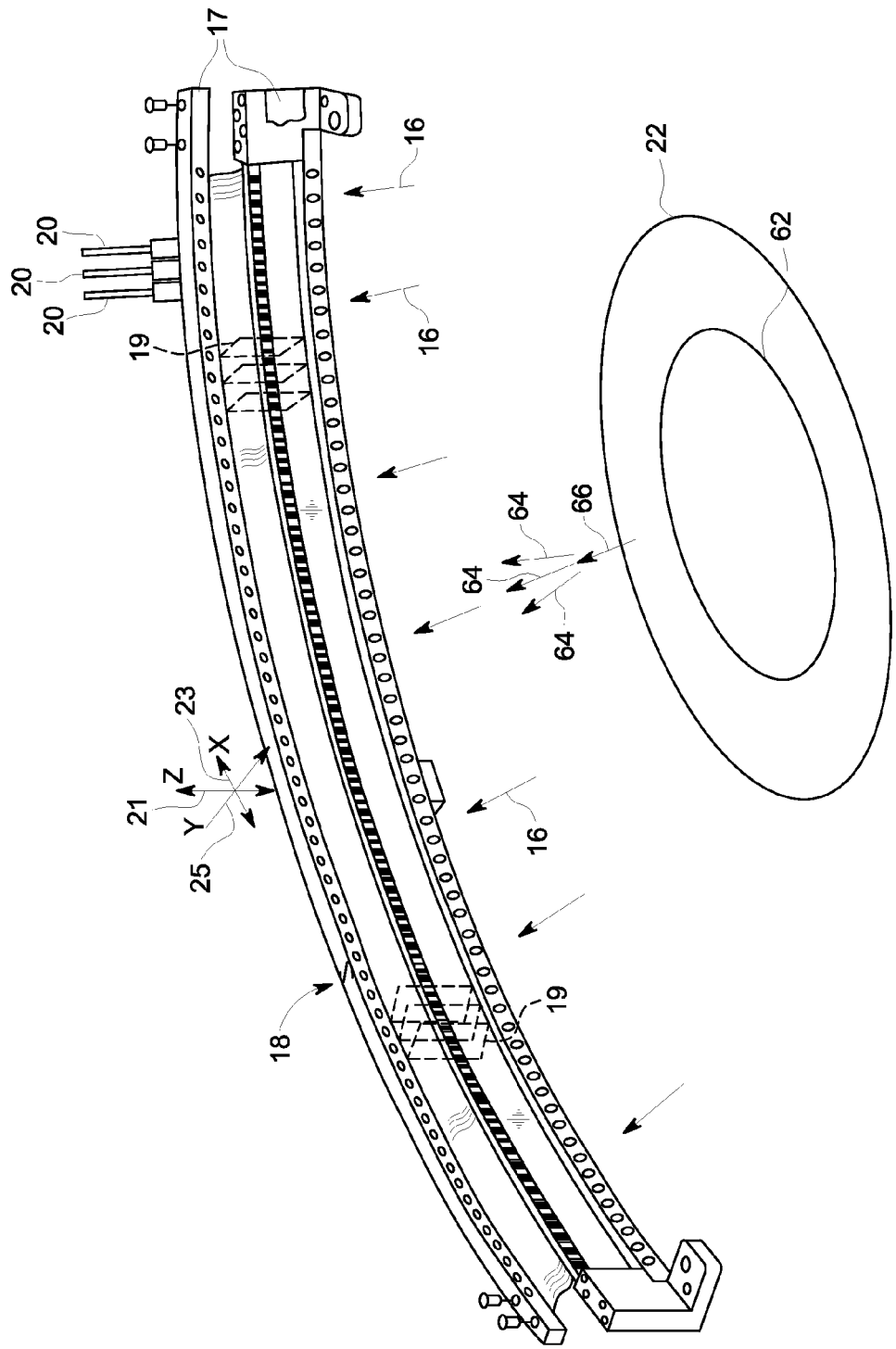
FIG. 3 is a perspective view of one embodiment of a CT system detector array.

As shown in FIG. 3, detector assembly 18 includes rails 17. Commonly, detector assembly 18 may include collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12. Thus, consistent with FIGS. 1 and 2, z-direction 21 (or slice direction), x-direction 23 (or channel direction), and y-direction 25 are illustrated. However, as will be further discussed, in lieu of plates 19, collimation may be provided instead, and according to embodiments of the invention, by collimator 11—positioned as illustrated in FIGS. 1 and 2.

Figure 4:
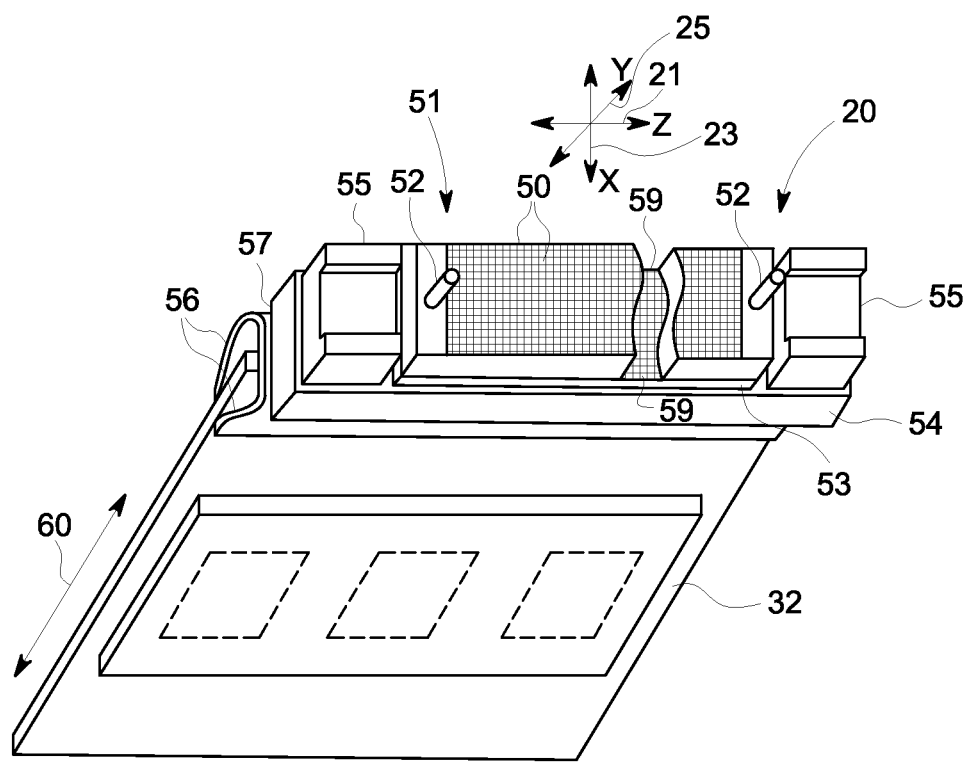
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal. Consistent with the earlier discussion, z-direction 21 defines also a slice direction and, as understood in the art, the number of detector elements 50 positioned along z-direction 21 and in detector 20 defines the number of imaging slices obtainable in an imaging system, such as imaging system 10 of FIGS. 1 and 2. Typically, the number of slices or detector elements 50 along z-direction 21 may be 16, 64, or 256. However, it is contemplated that the invention is not to be so limited, and that any number of slices may be collimated, according to the invention. X-direction 23, or channel direction, is also illustrated as it relates to detector 20. Typically, as stated, each detector 20 includes 16 detector elements 50 in x-direction 23, and there are typically 57 such detectors 20 positioned in detector assembly 18. However, it is contemplated that the invention is not to be so limited, and that any number of channels may be collimated, according to the invention. Y-direction 25 is illustrated, having a direction that is generally parallel 60 with DAS 32.

Referring back to FIG. 3, three exemplary detectors 20 (also referred to as detector modules) are illustrated therein (of the 57 modules described above, for example). During imaging of, for instance, patient 22 of FIGS. 1 and 2, a field-of-view (FOV) 62 may be imaged by obtaining imaging data from the detectors 20, mounted on detector assembly 18. Thus, as gantry 12 is rotated, x-rays 16 emit from source 14, through patient 22, and are received by detectors 20. Typically, imaging data is obtained of FOV 62 as either a helical or an axial scan is performed, as known in the art. As also known in the art, channels placed near the centermost locations 64 of detector assembly 18 along x-direction 23 are typically the most sensitive to misalignment of detectors 20, scatter, and the like. Commonly, the very centermost channel, at the center of detector assembly 18 along x-direction 23, is defined as the iso-channel or iso-center, which receives x-rays that pass along a centermost ray 66 to detector assembly 18. For further illustration, referring back to FIG. 2, ray 66 shows centermost ray 66 passing generally through center-of-rotation 24.

Figure 5:
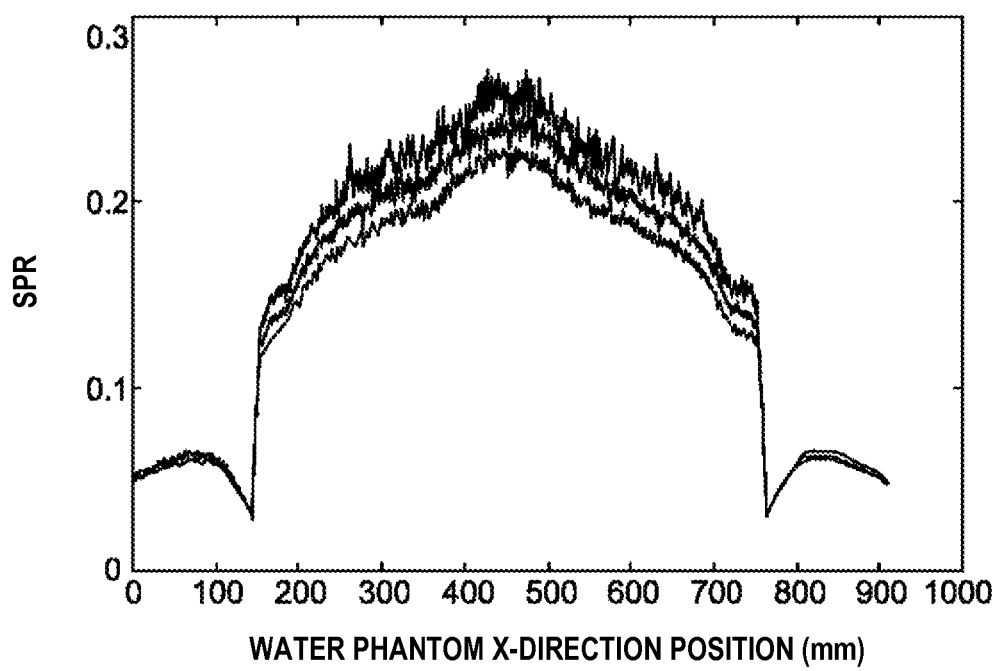
FIG. 5 depicts a measured scatter-to-primary (SPR) ratio for an exemplary phantom.

In general, the scattered radiation level is higher near the center of FOV 62 in x-direction 23, and falls off moving away from iso-center 66 along x-direction 23. For illustration, FIG. 5 depicts a measured scatter-to-primary ratio (SPR) for a 35 cm water phantom collected on a VCT system with 40 mm detector coverage, as an example. The scatter was calculated by taking the difference between the measurement obtained with a 40 mm z-collimation and a 5 mm z-collimation. The amount of scatter present in the 5 mm measurement is assumed to be negligible. A 35 cm water phantom is used to simulate a "typical" adult abdominal scan. It is clear that SPR is a maximum at ray 66, at the center of detector assembly 18 along x-direction 23, and falls off as a function of the distance from the iso-channel that occurs at ray 66. However, one objective for improving scatter rejection is to realize an approximately uniform SPR over at least some portions of the object to be imaged, traversing particularly in x-direction 23.

The above discussion leads to the observation that the scatter rejection capability of the system can be location dependent if the objective is to maintain an approximately uniform SPR. In other words, it is feasible to reduce the scatter rejection of the detector edge channels (in x-direction 23) without significantly impacting the overall performance of the CT system. As mentioned 2D collimation typically has an observably higher scatter rejection capability than 1D collimation, and the cost of the 2D collimation can also be much higher. Thus, to optimize image quality performance with cost, a hybrid post-patient collimation system is included in system 10, according to the invention, in which the center portion of the detector (in x-direction 23) is made of 2D collimation modules and the edge portion (both sides along either x-direction 23 from isocenter ray 66) of the detector is made of 1D collimation modules. According to the invention, the size of the 2D collimation can be determined based on phantom experiments and clinical studies or the field of view where a high SPR is needed. For example, one preferred embodiment is to make the center region corresponding to a 30 cm FOV that consists of 2D collimation, with the remaining portions 1D collimation. The aspect ratio the 1D and 2D collimation can be adjusted to minimize the difference in SPR at the interface of the 1D and 2D collimation.

Figure 6:
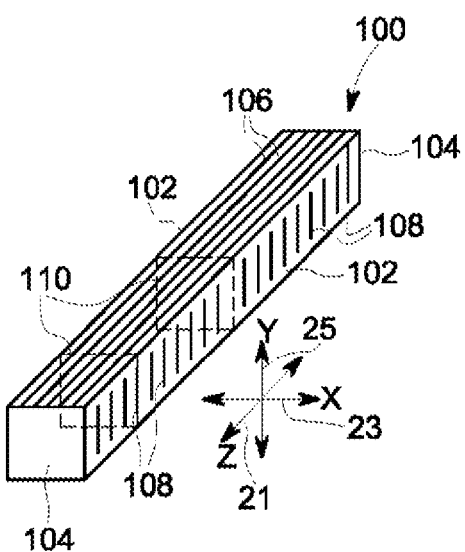
FIG. 6 illustrates a perspective view of a modular collimator assembly that may include either 1D or 2D collimation.

As known in the art, 1D and 2D collimators may be fabricated by a number of known methods, to include molding and the use of plates. Thus, it is contemplated that any collimator fabrication technique is applicable to the disclosed invention that will provide collimation as discussed with respect to FIGS. 1 and 2 as collimator assembly 11. In one example, referring to FIG. 6, a modular collimator assembly 100 is illustrated having sidewalls 102 and endwalls 104. Modular collimator assembly 100, illustrated with respect to z-direction 21, x-direction 23, and y-direction 25, includes channel plates 106 positioned in a y-z plane that is generally parallel with both z-direction 21 and y-direction 25. As known in the art, each y-z plane, and respective channel plates 106 positioned therein, are angled with respect to one another such that they point generally toward a common focal spot emitting from, for instance, x-ray source 14 of FIGS. 1 and 2.

Modular collimator assembly 100 may also include slots 108 positioned in sidewalls 102, with channel plates 106 having respective slots therein (not illustrated), such that slice plates 110 may be positioned therein, in an x-y plane (that is generally parallel to both x-direction 23 and y-direction 25). As known in the art, each x-y plane, and respective slice plates 110, are angled with respect to one another such that they point generally toward a common focal spot emitting from, for instance, x-ray source 14 of FIGS. 1 and 2 (and FIG. 7, below). Thus, modular collimator assembly 100 may be fabricated having 1D collimation in the y-z plane, and modular collimator assembly 100 may be fabricated having 2D collimation by adding slice plates 110 in the x-y plane. Further, it is contemplated that different plate heights, in y-direction 25 (or generally parallel to x-rays 16), may be included for channel plates 106 and/or slice plates 110—either within a modular collimator assembly 100, or in different modules that may be used to assemble collimator assembly 11, to provide a variation in aspect ratios thereof. And, it is contemplated that the number of slots 108 may only be partially populated with slice plates 110 (for example, every other slice). As such, modular collimator assembly 100 includes flexibility in design to provide improved scatter rejection and cost savings in an overall system, according to the invention. Further, modular collimator assembly 100 may be attached to a detector structure, such as detector assembly 18 of FIGS. 1-3, to form collimator assembly 11. Although collimator assembly 11 is illustrated as being attached to a concave side of detector assembly 18, it is contemplated that collimator assembly may be placed on the convex side thereof, or between rails 17 of FIG. 3, in lieu of collimating plates 19 illustrated therein.

Figure 7:
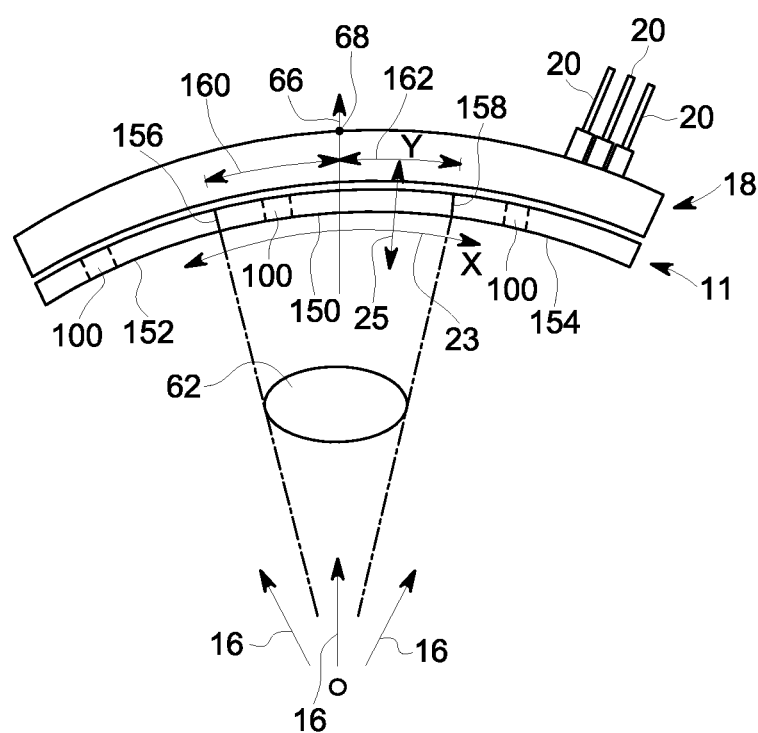
FIG. 7 illustrates a plan view of a detector assembly, having collimation regions, according to an embodiment of the invention.

Referring now to FIG. 7, a plan view of detector assembly 18, having detectors 20 placed thereon, includes x-ray collimation provided by collimator assembly 11, according to an embodiment of the invention. Detector assembly 18 includes centermost ray 66 which passes to a centermost channel or an iso-channel 68 of a detector 20 (not illustrated, but positioned to receive x-rays 16 passing along centermost ray 66). Collimator assembly 11 includes a first region 150 a second region 152, and a third region 154. Each region 150-154 includes modular collimator assemblies 100. However, as stated, modular collimator assemblies 100 may be fabricated in different fashions such that some include 2D collimation and some include only 1D collimation. Thus, according to this embodiment, first region 150 includes collimation for iso-channel 68 and is fabricated having collimator assemblies 100 that include slice plates 110, thus providing 2D collimation in both the y-z plane and the x-y plane. Also according to this embodiment, second and third regions 152, 154 are fabricated having collimator assemblies 100 that do not include slice plates 110, thus providing 1D collimation in only the y-z plane. As such, first region 150 includes modules 100 having two-dimensional arrays of apertures that are formed by plates 106 and 110, and second and third regions 152, 154 include modules 100 having one-dimensional arrays of apertures that are formed by plates 106.

First region 150 and second region 152 are separated by a first boundary 156, and first region 150 and third region 154 are separated by a second boundary 158. Boundaries 156, 158 are defined as a location along x-direction 23, from iso-channel 68, between 2D modules and 1D modules. Thus, first boundary 156 is positioned a first distance 160, along x-direction 23, from iso-channel 68, and second boundary 158 is positioned a second distance 162, along x-direction 23, from iso-channel 68. According to one embodiment, boundaries 156, 158 are selected to correspond symmetrically with respect to iso-channel 68 or to a FOV, such as FOV 62. However, the invention is not to be so limited, and boundaries 156, 158 may be asymmetrically selected according to any criteria, such as based on cost, empirical studies, or imaging procedure to be performed, as examples. Thus, at boundaries 156, 158, an abrupt change in aspect ratio occurs.

As stated, first region 150, and second and third regions 152/154 may include modules 100 that have differing aspect ratios therein and may have either one-dimensional collimating arrays, two-dimensional arrays, or a combination thereof. In the following illustrations, it is to be understood that the plate spacing, plate heights, and resultant aspect ratios are illustrated for symbolic purposes and do not include all channels in x-direction 23 or slices in z-direction 21 as is typically found in an imaging system. That is, regions are illustrated that correspond generally to detector assembly 18 discussed above, but the one-dimensional and two-dimensional arrangements are illustrated as such in order to convey the various embodiments of the invention.

Figure 8:
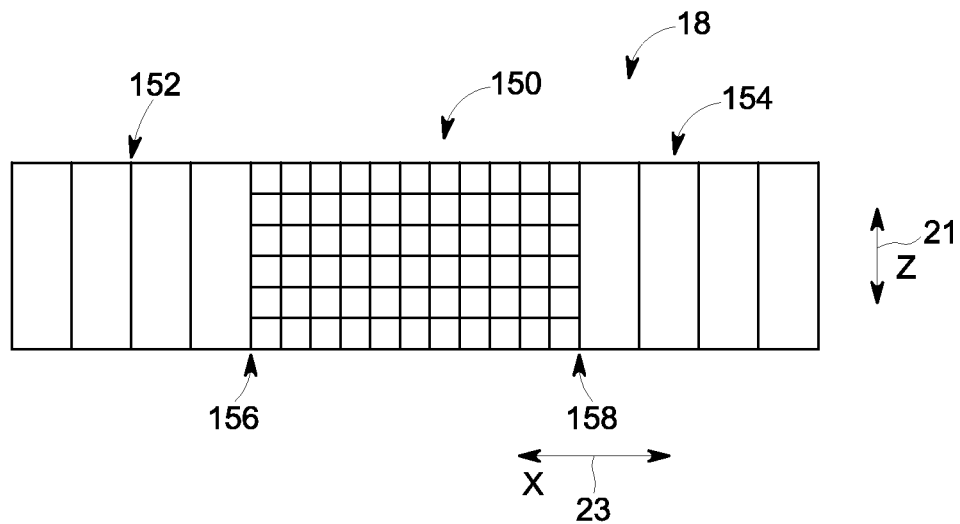
FIGS. 8-11 illustrate a detector assembly according to embodiments of the invention.

FIG. 8 illustrates a plan view of detector assembly 18 according to one embodiment of the invention. In this embodiment, first region 150 includes a two-dimensional array of plates, providing collimation in both x-direction 23 and z-direction 21. Second and third regions 152, 154 provide collimation in x-direction 23 only. Further, plate spacing in second and third regions 152, 154 having the one-dimensional arrangement is greater than plate spacing in first region 150 having the two-dimensional arrangement.

Figure 9:
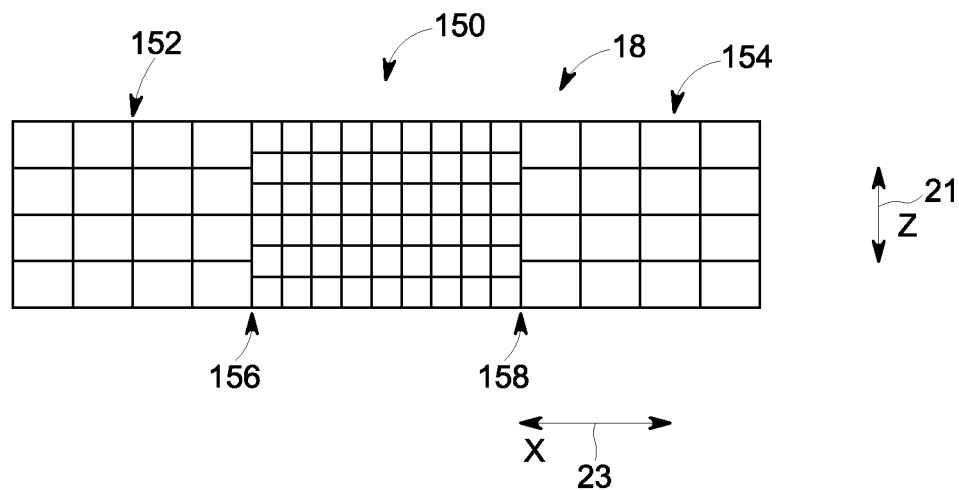

FIG. 9 illustrates a plan view of detector assembly 18 according to another embodiment of the invention. In this embodiment, first region 150 includes a two-dimensional array of plates, providing collimation in both x-direction 23 and z-direction 21. Second and third regions 152, 154 provide collimation, as well, in both x-direction 23 and z-direction 21. However, in this embodiment the aspect ratio between first region 150 and second and third regions 152, 154 is different. That is, first region 150 has smaller apertures than regions 152, 154.

Figure 10:
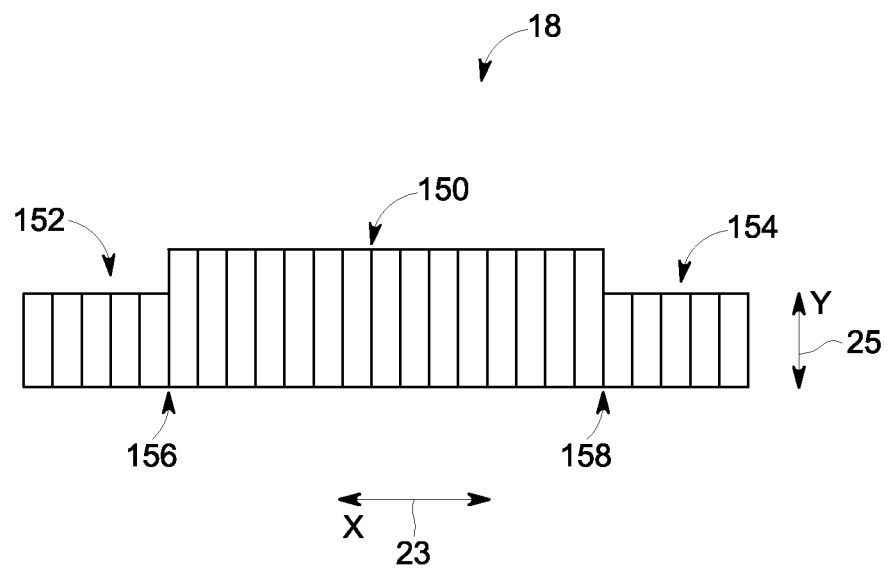

FIG. 10 illustrates a side view of detector assembly 18 (not having an arc, for simplicity of illustration, as is shown in FIG. 7, for instance). In this embodiment, plate height (as measured along y-direction 25 and generally along a direction that x-rays pass from source to detector) is greater in region 150 than in regions 152, 154. However, in this embodiment the spacing between plates is the same in all regions. That is, plate spacing in region 150 in this embodiment is the same as in regions 152, 154. Nevertheless, because plate height differs between the regions, it is evident that the aspect ratios are different in the different regions. Thus, according to the invention, region 150 may include a one-dimensional or a two-dimensional array of plates. Likewise, regions 152, 154 may also include one-dimensional or two-dimensional arrays.

Figure 11:
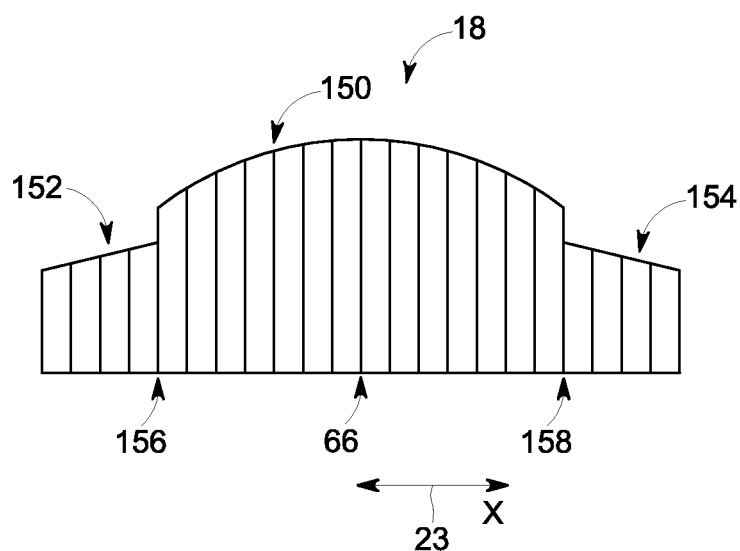

FIG. 11 illustrates a side view of detector assembly 18 which, similar to FIG. 10, is not illustrated on an arc for simplicity of illustration of the embodiment. In this embodiment, plate height (as measured along y-direction 25) is variable along x-direction 23, with the highest plate being positioned at a centermost channel where centermost ray 66 passes therethrough. And, although plate spacing of region 150 is shown as the same as plate spacing of regions 152, 154, it is understood that plate spacing may differ from region to region. Further, it is to be understood that each region 150, 152, 154 may include a one-dimensional array of plates along x-direction 23, or two-dimensional arrays of plates in both x-direction 23 and z-direction 21.

Despite the adjustment of the aspect ratios near boundaries 156, 158 of different collimation types, it is unavoidable that differences between SPRs exist at the boundaries 156, 158. Thus, potential artifacts can be introduced due to the discontinuities in SPR. However, several remedies can be utilized to suppress the discontinuity.

Figure 12:
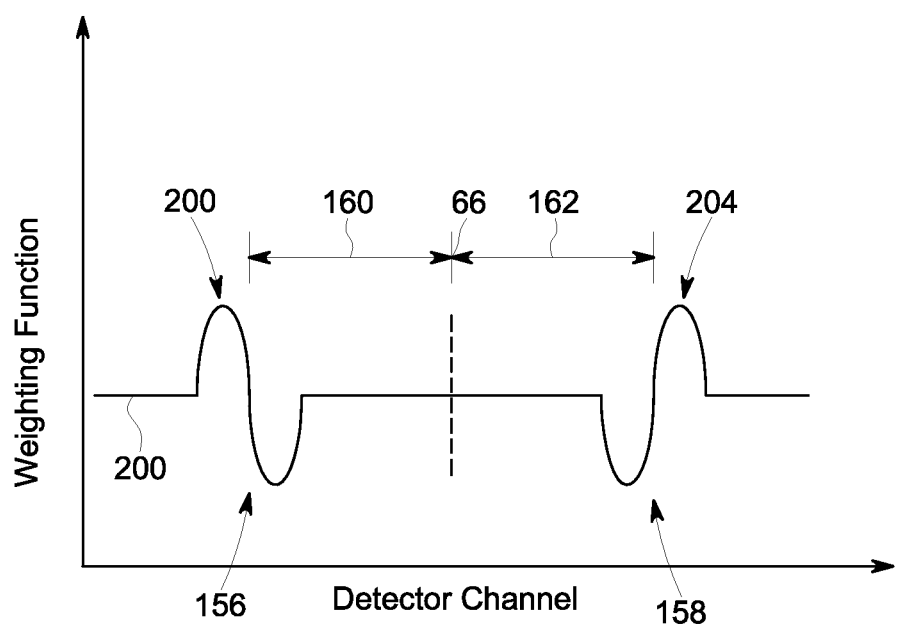
FIG. 12 illustrates an example of a weighting function for scatter correction to correct for discontinuities between 1D and 2D collimator boundaries.

As known in the art, scatter correction algorithms may be applied during reconstruction by for instance image reconstructor 34 of FIG. 2, having a strength of correction that is adjustable. Thus, one approach to correcting discontinuities of SPR at boundaries 156, 158 is to decrease the strength of the scatter correction algorithm in the 2D region as the 2D to 1D boundary is approached, and at the same time increase the strength of the scatter correction in the 1D region as the 1D to 2D boundary is approached. Thus, referring to FIG. 12, one example of a weighting function is illustrated that may be applied using image reconstructor 34 to correct for such discontinuities by adjusting weighting function 200, accordingly. That is, weighting function 200 may include a first adjustment function 202 that occurs at first boundary 156 and a first distance 160 from centermost ray 66, and weighting function 200 may include a second adjustment function 204 that occurs at second boundary 158 and a second distance 162 from centermost ray 66—but in a negative direction, or a direction opposite that of first distance 160. Thus, during the reconstruction process, a weighting function is used to suppress the contribution of the transition region to the final image, and FIG. 8 depicts one example of such a function.

Another approach is to locate 1D to 2D collimation boundaries 156, 158 asymmetrically relative to the iso-channel. That is, the impact of the discontinuity between the 1D and 2D collimation may be reduced or minimized by ensuring that first distance 160 and second distance 162 are different from one another in their respective lengths. And, in addition to the asymmetric lengths of distances 160, 162, during the reconstruction process, a weighting function, such as that discussed above with respect to FIG. 8, may be used to suppress the contribution of the transition region to the final image.

Figure 13:
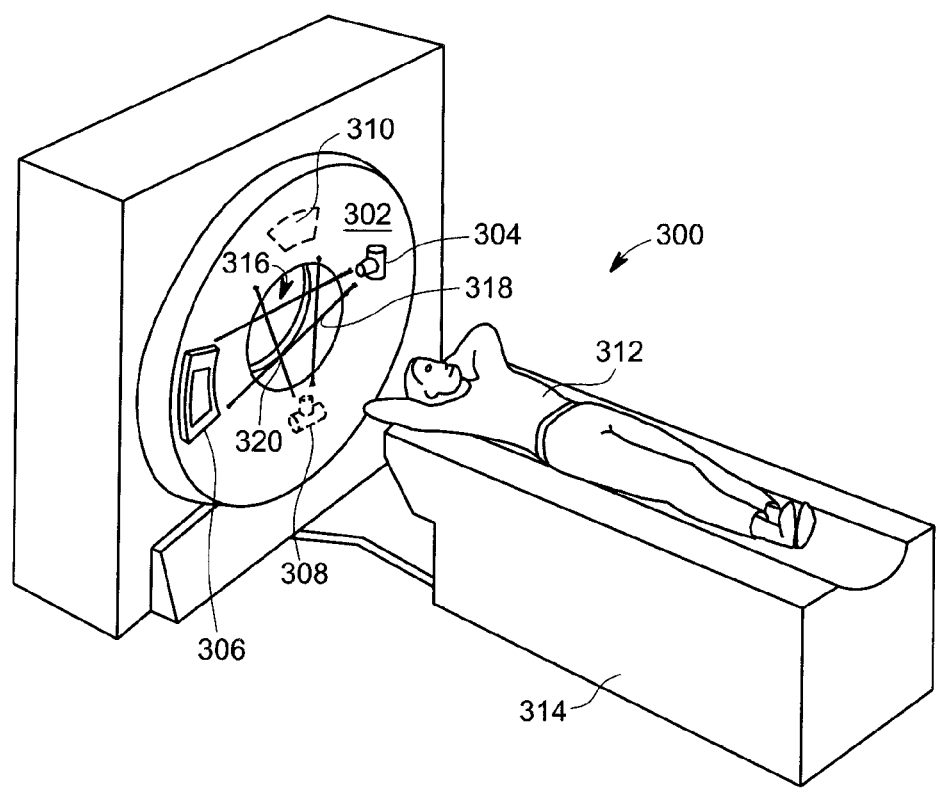
FIG. 13 illustrates a CT imaging system having two sources and two detector assemblies that incorporate embodiments of the invention.

FIGS. 13 illustrates a pictorial view of a two-tube and two-detector CT system 300 that incorporates embodiments of the invention. System 300 includes a gantry 302 representative of a "third generation" CT scanner. Gantry 302 has a first x-ray source 304 that projects a beam of x-rays toward a first detector assembly 306 on the opposite side of gantry 202. Gantry 302 also has a second x-ray source 308 that projects a beam of x-rays toward a second detector assembly 310. Patient 312 is positioned on motorized table 314 and passed through opening 316. Imaging data may be simultaneously taken of patient 312 using both source/detector pairs (i.e., source 304/detector 306 and source 308/detector 310). And, such data may be obtained using sources at different energy levels (i.e., 80 kVp and 140 kVp) for dual energy imaging, or at the same energy level for an increased temporal resolution as compared to a single source/detector system. Detectors 306 and 310 may be fabricated according to embodiments of the invention. In fact, it is contemplated that first detector assembly 306 may be fabricated of any of the hybrid detector arrangements as mentioned above, and second detector assembly 310 may be fabricated of the same hybrid detector as 306, or a different of the embodiments herein disclosed. Thus, first source 304 may project a first beam 318 to first detector 306, and second source 308 may project a second beam 320 toward second detector 310. It is contemplated that system 300 may include control and other operation capabilities as described above with respect to FIGS. 1 and 2, For instance, it is contemplated one tube/detector pair has a two-dimensional array of collimation and the other tube/detector pair has a one-dimensional array of collimation. In another example, each tube/detector pair includes a two-dimensional collimator, wherein the aspect ratios of each are different from one another. In yet another example, each tube/detector pair may include a one-dimensional collimator, wherein the aspect ratios of each are different from one another.

Figure 14:
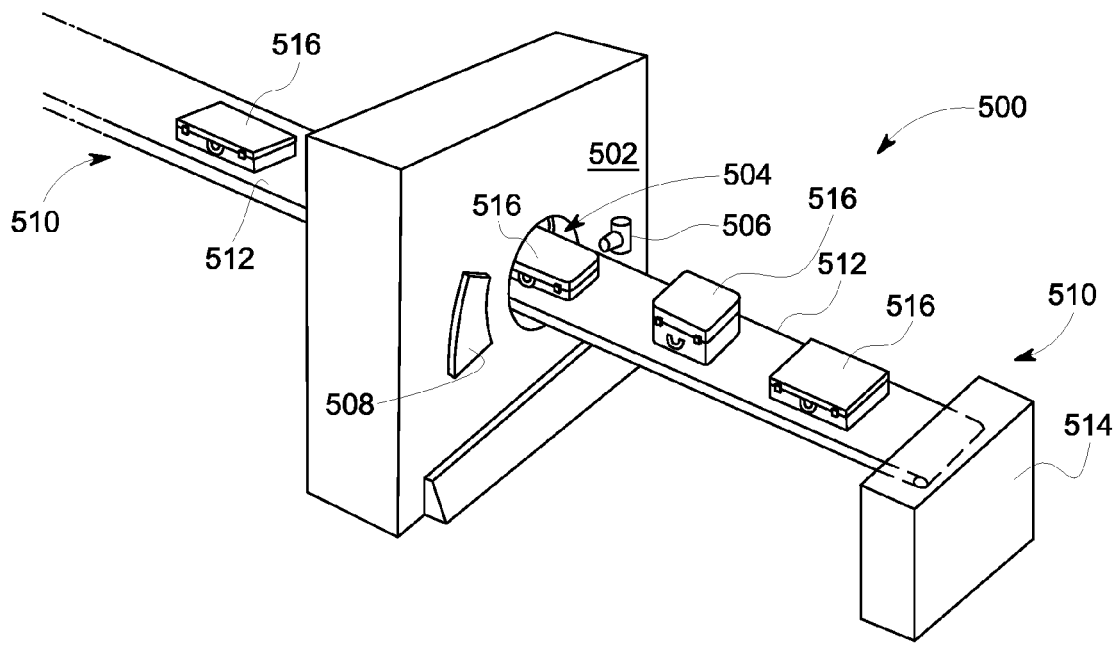
FIG. 14 is a pictorial view of a CT system for use with a non-invasive package inspection system.

Referring now to FIG. 14, package/baggage inspection system 500 includes a rotatable gantry 502 having an opening 504 therein through which packages or pieces of baggage may pass. The rotatable gantry 502 houses a high frequency electromagnetic energy source 506 as well as a detector assembly 508 having scintillator arrays comprised of scintillator cells similar to that shown in FIG. 4. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc.

A technical contribution for the disclosed method and apparatus is that it provides for a computer implemented apparatus for scatter reduction for CT imaging.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

According to one embodiment, a collimator for an imaging system includes a first region comprising a first one-dimensional array of apertures along a channel direction, and a second region comprising a second one-dimensional array of apertures along the channel direction, wherein an aspect ratio of the apertures of the first region is greater than an aspect ratio of the second region.

According to another embodiment, a method of forming a collimator for an imaging system includes forming a first one-dimensional array of apertures, forming a second one-dimensional array of apertures having an aspect ratio that is different from that of the first one-dimensional array of apertures, and attaching the first one-dimensional array of apertures and the second one-dimensional array of apertures to a support structure.

According to yet another embodiment, a CT system includes a rotatable gantry having an opening to receive an object to be scanned, a first high frequency electromagnetic energy projection source configured to project a high frequency electromagnetic energy beam toward the object, a first scintillator array having a plurality of scintillator cells wherein each cell is configured to detect high frequency electromagnetic energy passing through the object, and a first photodiode array optically coupled to the scintillator array and comprising a plurality of photodiodes configured to detect light output from a corresponding scintillator cell. The system includes an image reconstructor coupled to the first photodiode array and configured to reconstruct an image of the object from the first photodiode array outputs, and a first collimator positioned between the first high frequency electromagnetic energy projection source and the scintillator. The first collimator includes a first sub-assembly comprised of a first one-dimensional array of openings, and a second sub-assembly comprised of a second one-dimensional array of openings, wherein an aspect ratio of the second one-dimensional array of openings is less than an aspect ratio of the first one-dimensional array of openings. The system also includes a computer programmed to obtain imaging data of the object, and reconstruct an image of the object using the imaging data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. A collimator for an imaging system comprising:
a first region comprising a plurality of planar collimating plates arranged to form a first one-dimensional array of apertures along an x-direction of the imaging system;
a second region comprising a plurality of planar collimating plates arranged to form a second one-dimensional array of apertures along the x-direction, wherein an aspect ratio of the apertures of the first region is greater than an aspect ratio of the second region; and a third region comprising a plurality of planar collimating plates arranged to form a third one-dimensional array of apertures along the x-direction;

wherein a first boundary is formed between the first region and the second region and a second boundary is formed between the first region and the third region;

wherein the first region includes a centermost channel in the x-direction, such that the first region collimates x-rays that pass through an isocenter of the imaging system;

wherein the second region is offset from the first region in the x-direction such that the second region does not include the centermost channel but is positioned to collimate x-rays that pass off-center from the isocenter of the imaging system; and wherein the first boundary and the second boundary are asymmetrically positioned in the x-direction such that the first boundary is a distance from the centermost channel that is different from a distance between the second boundary and the centermost channel.

2. The collimator of claim 1 wherein:
the first region comprises a plurality of first modules having the first one-dimensional array of apertures; and
the second region comprises a plurality of second modules having the second one-dimensional array of apertures.

3. The collimator of claim 1 wherein at least one aperture in the x-direction of the second region is wider than the apertures of the first one-dimensional array of apertures in the x-direction of the first region.

4. The collimator of claim 1 wherein:
apertures in at least one of the first and second regions are formed of materials having a varying height along the x-direction; and
the height is defined to be in a direction that is generally parallel to primary x-rays passing therethrough that emit from a focal spot of an x-ray source in a CT imaging system.

5. The collimator of claim 1 wherein a spacing of the collimating plates in the first region is less than a spacing of the collimating plates in one of the second and third regions.

6. The collimator of claim 5 wherein the first one-dimensional array of apertures also includes collimating plates along a z-direction such that the first region is formed of a two-dimensional array of apertures.

7. The collimator of claim 6 wherein the second one-dimensional array of apertures also includes collimating plates along a z-direction such that the second region is formed of a two-dimensional array of apertures.

8. The collimator of claim 4 wherein an aperture having the greatest collimating plate height is a centermost channel in the x-direction.

9. The collimator of claim 3 wherein each of the plurality of collimating plates in the first region is positioned with a varying angle with respect to one another such that each aperture formed is generally aimed toward a focal spot of an x-ray source of a CT imaging system.

10. A method of forming a collimator for an imaging system comprising:
arranging a plurality of collimating plates in a y-z plane to form a first one-dimensional array of apertures;
arranging a plurality of collimating plates in a y-z plane to form a second one-dimensional array of apertures having an aspect ratio that is different from that of the first one-dimensional array of apertures; and attaching the first one-dimensional array of apertures and the second one-dimensional array of apertures to a support structure;

wherein the first one-dimensional array of apertures includes a centermost channel in an x-direction at an isocenter of the imaging system;

wherein the second one-dimensional array of apertures is offset from the first one-dimensional array of apertures in the x-direction such that the second one-dimensional array of apertures does not include the centermost channel;

wherein forming the first one-dimensional array of apertures includes forming a plurality of first one-dimensional modules, the first one-dimensional modules forming the first one-dimensional array of apertures;

wherein forming the second one-dimensional array of apertures includes forming a second plurality of second one-dimensional modules, the second one-dimensional modules forming the second one-dimensional array of apertures; and wherein attaching the first one-dimensional array of apertures and the second one-dimensional array of apertures to the support structure comprises attaching the first one-dimensional modules and the second one-dimensional modules to the support structure.

11. The method of claim 10 further comprising arranging a plurality of collimating plates in a x-y plane to transform the first one-dimensional array of apertures into a two-dimensional array of apertures.

12. The method of claim 10 comprising:
arranging a plurality of collimating plates in a y-z plane to form a third one-dimensional array of apertures;
attaching the first one-dimensional array of apertures to the support structure such that a centermost detector channel of the imaging system, in a x-direction of the imaging system, is collimated by an aperture of the first one-dimensional array of apertures, wherein the x-direction is a direction that is transverse to a z-direction of the imaging system;
attaching the second one-dimensional array of apertures to the support structure beginning at a first distance in the x-direction from the centermost detector channel of the imaging system; and
attaching the third one-dimensional array of apertures to the support structure beginning at a second distance in a negative x-direction from the centermost detector channel of the imaging system.

13. The method of claim 12 wherein the first distance is different in length from the second distance.

14. The method of claim 12 wherein at least one aperture of the first and third one-dimensional array of apertures is formed of collimating plates that are positioned further apart than collimating plates in the channel direction that are used to form the second one-dimensional array of apertures.

15. The method of claim 12 wherein forming the first and third one-dimensional arrays of apertures and forming the second one-dimensional array of apertures comprises forming the apertures having an aspect ratio that is varied as a function of their position on the support structure.

16. The method of claim 15 comprising selecting the aspect ratio for the apertures based on an assumed scatter-to-primary (SPR) ratio of the collimator.

17. A CT system comprising:
a rotatable gantry having an opening to receive an object to be scanned, the rotatable gantry being configured to rotate circumferentially in an x-direction;

a first high frequency electromagnetic energy projection source configured to project a high frequency electromagnetic energy beam toward the object;

a first scintillator array having a plurality of scintillator cells wherein each cell is configured to detect high frequency electromagnetic energy passing through the object;

a first photodiode array optically coupled to the scintillator array and comprising a plurality of photodiodes configured to detect light output from a corresponding scintillator cell;

an image reconstructor coupled to the first photodiode array and configured to reconstruct an image of the object from the first photodiode array outputs;

a first collimator positioned between the first high frequency electromagnetic energy projection source and the scintillator, the first collimator comprising:

a first sub-assembly comprised of a plurality of planar collimating plates arranged to form a first one-dimensional array of openings; and a second sub-assembly comprised of a plurality of planar collimating plates arranged to form a second one-dimensional array of openings, wherein an aspect ratio of the second one-dimensional array of openings is less than an aspect ratio of the first one-dimensional array of openings; and a computer programmed to:
obtain imaging data of the object;
apply a scatter correction algorithm to correct the imaging data of the object;
weight a strength of the scatter correction algorithm as a function of a distance of data acquired from a center-most channel within the first scintillator array; and
reconstruct an image of the object using the corrected imaging data;

wherein the second sub-assembly is offset from the first sub-assembly in the x-direction.

18. The CT system of claim 17 wherein the first sub-assembly includes collimating plates positioned in a z-direction such that the first sub-assembly is comprised of a two-dimensional array of apertures.

19. The CT system of claim 17 wherein the CT system further comprises:

a second high frequency electromagnetic energy projection source configured to project a high frequency electromagnetic energy beam toward the object;

a second scintillator array having a plurality of scintillator cells wherein each cell is configured to detect high frequency electromagnetic energy passing through the object;

a second photodiode array optically coupled to the scintillator array and comprising a plurality of photodiodes configured to detect light output from a corresponding scintillator cell;

an image reconstructor coupled to the second photodiode array and configured to reconstruct the image of the object from the second photodiode array outputs; and a second collimator positioned between the second high frequency electromagnetic energy projection source and the scintillator 20. The CT system of claim 19 wherein the first and second sub-assemblies have a first aspect ratio and the second collimator has apertures having a second aspect ratio that is different from the first aspect ratio.

21. The CT system of claim 20 wherein the first and second sub-assemblies, and the second collimator, include plates positioned in a z-direction such that two-dimensional grids are formed in each of the first and second collimators.

22. The CT system of claim 19 wherein the second collimator comprises:

a third sub-assembly comprised of a third one-dimensional array of openings; and a fourth sub-assembly comprised of a fourth one-dimensional array of openings, wherein an aspect ratio of the third one-dimensional array of openings is less than an aspect ratio of the fourth one-dimensional array of openings.

23. The CT system of claim 22 wherein at least one of the third sub-assembly and the fourth sub-assembly include collimating plates in a z-direction such that at least one of the third and fourth sub-assemblies forms a two-dimensional array of openings.

24. The CT system of claim 22 comprising a fifth sub-assembly comprised of a fifth one-dimensional array of openings; wherein:

the first sub-assembly is positioned to collimate x-rays that pass through an isocenter of the CT system;

the second sub-assembly is positioned to collimate x-rays that pass off-center from the isocenter in the x-direction on a first side of the first sub-assembly; and the fifth sub-assembly is positioned to collimate x-rays that pass off-center from the isocenter in the x-direction on a second side of the first sub-assembly that is opposite the first side.

25. The CT system of claim 24 wherein:

the first sub-assembly is comprised of a plurality of two-dimensional modules having a two-dimensional array of openings;

the second sub-assembly is comprised of a first plurality of one-dimensional modules having the second one-dimensional array of openings; and the fifth sub-assembly is comprised of a second plurality of one-dimensional modules having the fifth one-dimensional array of openings.

26. The CT system of claim 24 wherein the second and fifth sub-assemblies are positioned asymmetrically on the CT system such that the first sub-assembly is positioned beginning at a first distance from the isocenter on the first side of the first sub-assembly, and such that the fifth sub-assembly is positioned beginning at a second distance from the isocenter on the second side of the first sub-assembly.

27. The CT system of claim 26 wherein the openings in the second and third sub-assemblies have openings that are wider, along the x-direction, than openings in the first sub-assembly along the x-direction.

28. The CT system of claim 26 wherein the openings in the first sub-assembly at the isocenter have an aspect ratio that is greater than all other aspect ratios of the remaining openings in the collimator, and the aspect ratio decreases monotonically in the apertures along the x-direction.

29. A collimator for an imaging system comprising:

a first region comprising a plurality of planar collimating plates arranged to form a first one-dimensional array of apertures along an x-direction of the imaging system;

a second region comprising a plurality of planar collimating plates arranged to form a second one-dimensional array of apertures along the x-direction, wherein an aspect ratio of the apertures of the first region is greater than an aspect ratio of the second region; and a third region comprising a plurality of planar collimating plates arranged to form a third one-dimensional array of apertures along the x-direction;

wherein a first boundary is formed between the first region and the second region and a second boundary is formed between the first region and the third region;

wherein the first region includes a centermost channel in the x-direction, such that the first region collimates x-rays that pass through an isocenter of the imaging system;

wherein the second region is offset from the first region in the x-direction such that the second region does not include the centermost channel but is positioned to collimate x-rays that pass off-center from the isocenter of the imaging system; and wherein at least one aperture in the x-direction of the second region is wider than the apertures of the first one-dimensional array of apertures in the x-direction of the first region.

30. A collimator for an imaging system comprising:

a first region comprising a plurality of planar collimating plates arranged to form a first one-dimensional array of apertures along an x-direction of the imaging system;

a second region comprising a plurality of planar collimating plates arranged to form a second one-dimensional array of apertures along the x-direction, wherein an aspect ratio of the apertures of the first region is greater than an aspect ratio of the second region; and a third region comprising a plurality of planar collimating plates arranged to form a third one-dimensional array of apertures along the x-direction;

wherein a first boundary is formed between the first region and the second region and a second boundary is formed between the first region and the third region;

wherein the first region includes a centermost channel in the x-direction, such that the first region collimates x-rays that pass through an isocenter of the imaging system;

wherein the second region is offset from the first region in the x-direction such that the second region does not include the centermost channel but is positioned to collimate x-rays that pass off-center from the isocenter of the imaging system; and wherein a spacing of the collimating plates in the first region is less than a spacing of the collimating plates in one of the second and third regions.

31. A CT system comprising:

a rotatable gantry having an opening to receive an object to be scanned, the rotatable gantry being configured to rotate circumferentially in an x-direction;

a first high frequency electromagnetic energy projection source configured to project a high frequency electromagnetic energy beam toward the object;

a first scintillator array having a plurality of scintillator cells wherein each cell is configured to detect high frequency electromagnetic energy passing through the object;

a first photodiode array optically coupled to the scintillator array and comprising a plurality of photodiodes configured to detect light output from a corresponding scintillator cell;

an image reconstructor coupled to the first photodiode array and configured to reconstruct an image of the object from the first photodiode array outputs;

a first collimator positioned between the first high frequency electromagnetic energy projection source and the scintillator, the first collimator comprising:
 a first sub-assembly comprised of a plurality of planar collimating plates arranged to form a first one-dimensional array of openings; and
 a second sub-assembly comprised of a plurality of planar collimating plates arranged to form a second one-dimensional array of openings, wherein an aspect ratio of the second one-dimensional array of openings is less than an aspect ratio of the first one-dimensional array of openings; and a computer programmed to:
 obtain imaging data of the object; and
 reconstruct an image of the object using the imaging data;

wherein the second sub-assembly is offset from the first sub-assembly in the x-direction; and wherein the CT system further comprises:
 a second high frequency electromagnetic energy projection source configured to project a high frequency electromagnetic energy beam toward the object;
 a second scintillator array having a plurality of scintillator cells wherein each cell is configured to detect high frequency electromagnetic energy passing through the object;
 a second photodiode array optically coupled to the scintillator array and comprising a plurality of photodiodes configured to detect light output from a corresponding scintillator cell;.
 an image reconstructor coupled to the second photodiode array and configured to reconstruct the image of the object from the second photodiode array outputs; and
 a second collimator positioned between the second high frequency electromagnetic energy projection source and the scintillator;

wherein the first and second sub-assemblies have a first aspect ratio and the second collimator has apertures having a second aspect ratio that is different from the first aspect ratio.

* * * * *

UNITED STATES PATENT AND TRADEMARK OFFICE
CERTIFICATE OF CORRECTION

| | | |
|---|---|---|
| PATENT NO. | : 8,831,180 B2 | Page 1 of 1 |
| APPLICATION NO. | : 13/198283 | |
| DATED | : September 9, 2014 | |
| INVENTOR(S) | : Hsieh et al. | |

It is certified that error appears in the above-identified patent and that said Letters Patent is hereby corrected as shown below:

In the Claims,

Col. 11, line 55 (Claim 9), delete "claim 3" and substitute therefore -- claim 1 --.

Col. 13, line 61 (Claim 19), delete "the scintillator" and substitute therefore -- the scintillator. --.

Signed and Sealed this
Tenth Day of February, 2015

Michelle K. Lee
*Deputy Director of the United States Patent and Trademark Office*